(12) United States Patent
Cole

(10) Patent No.: US 7,311,711 B2
(45) Date of Patent: Dec. 25, 2007

(54) SURGICAL DISTRACTOR FRAME

(76) Inventor: J. Dean Cole, 500 Lakeview Dr., Orlando, FL (US) 32804

( * ) Notice: Subject to any disclaimer, the term of this patent is extended or adjusted under 35 U.S.C. 154(b) by 0 days.

(21) Appl. No.: 10/326,655

(22) Filed: Dec. 21, 2002

(65) Prior Publication Data

US 2003/0120273 A1   Jun. 26, 2003

Related U.S. Application Data

(60) Provisional application No. 60/342,963, filed on Dec. 21, 2001.

(51) Int. Cl.
*A61B 17/00* (2006.01)
*A61F 4/00* (2006.01)

(52) U.S. Cl. ............... 606/57; 606/54; 606/59
(58) Field of Classification Search ........... 606/57, 606/53, 54, 55, 56, 58, 59, 102, 105; 600/105, 600/230
See application file for complete search history.

(56) References Cited

U.S. PATENT DOCUMENTS

| | | | | |
|---|---|---|---|---|
| 1,869,726 A | * | 8/1932 | Youngren | 606/57 |
| 1,997,466 A | * | 4/1935 | Longfellow | 606/59 |
| 2,391,537 A | * | 12/1945 | Anderson | 606/59 |
| 2,497,626 A | * | 2/1950 | Persall | 606/54 |
| 3,993,055 A | | 11/1976 | Volkov et al. | |
| 4,112,935 A | | 9/1978 | Latypov et al. | |
| 4,185,623 A | | 1/1980 | Volkov et al. | |
| 4,220,146 A | | 9/1980 | Cloutier | |
| 4,271,832 A | | 6/1981 | Evans et al. | |
| 4,448,191 A | | 5/1984 | Rodnyansky et al. | |
| 4,483,334 A | | 11/1984 | Murray | |
| 4,502,473 A | | 3/1985 | Harris et al. | |
| 4,637,382 A | | 1/1987 | Walker et al. | |
| 4,733,657 A | * | 3/1988 | Kluger | 606/61 |
| 4,768,524 A | | 9/1988 | Hardy | |
| 4,957,495 A | * | 9/1990 | Kluger | 606/58 |
| 4,968,316 A | * | 11/1990 | Hergenroeder | 606/90 |
| 4,969,886 A | | 11/1990 | Cziffer et al. | |
| 5,002,547 A | | 3/1991 | Poggie et al. | |
| 5,020,525 A | | 6/1991 | Ewing et al. | |
| 5,062,850 A | | 11/1991 | MacMillan et al. | |
| 5,063,918 A | | 11/1991 | Guhl | |
| 5,100,403 A | | 3/1992 | Hotchkiss et al. | |
| 5,102,411 A | | 4/1992 | Hotchkiss et al. | |
| 5,116,338 A | | 5/1992 | Poggie et al. | |
| 5,156,605 A | | 10/1992 | Pursley et al. | |
| 5,250,050 A | | 10/1993 | Poggie et al. | |
| 5,312,403 A | | 5/1994 | Frigg | |
| 5,376,091 A | | 12/1994 | Hotchkiss et al. | |
| 5,415,660 A | | 5/1995 | Campbell et al. | |

(Continued)

*Primary Examiner*—Pedro Philogene
(74) *Attorney, Agent, or Firm*—Haynes and Boone, LLP

(57) ABSTRACT

A distractor frame comprises an upper pin, a lower pin positioned substantially parallel to the upper pin, a pair of adjustment mechanisms, wherein each adjustment mechanism couples to the upper pin and the lower pin such that each adjustment mechanism is positioned generally perpendicular to the upper and lower pins, wherein each adjustment mechanism comprises a shaft, a first pin connector for coupling the upper pin to the shaft, a threaded rod coupled to an end of the shaft, a cylindrical sleeve adapted for threadedly engaging the threaded rod, such that a portion of the shaft and a portion of the threaded rod may be positioned within the cylindrical sleeve, and a second pin connector coupled to the cylindrical sleeve for coupling the lower pin.

19 Claims, 4 Drawing Sheets

U.S. PATENT DOCUMENTS

| | | |
|---|---|---|
| 5,429,638 A | 7/1995 | Muschler et al. |
| 5,431,653 A | 7/1995 | Callaway |
| 5,437,668 A | 8/1995 | Aronson et al. |
| 5,451,225 A | 9/1995 | Ross et al. |
| 5,464,406 A | 11/1995 | Ritter et al. |
| 5,482,055 A | 1/1996 | Smith |
| 5,484,437 A | 1/1996 | Michelson |
| 5,505,732 A | 4/1996 | Michelson |
| 5,505,733 A | 4/1996 | Justin et al. |
| 5,540,695 A | 7/1996 | Levy |
| 5,630,814 A | 5/1997 | Ross et al. |
| 5,649,929 A | 7/1997 | Callaway |
| 5,669,914 A | 9/1997 | Eckhoff |
| 5,676,664 A | 10/1997 | Allard et al. |
| 5,676,665 A | 10/1997 | Bryan |
| 5,681,309 A | 10/1997 | Ross et al. |
| 5,690,633 A | 11/1997 | Taylor et al. |
| 5,704,939 A | 1/1998 | Justin |
| 5,709,683 A | 1/1998 | Bagby |
| 5,733,305 A | 3/1998 | Fleischmann |
| 5,755,803 A | 5/1998 | Haines et al. |
| 5,766,173 A * | 6/1998 | Ross et al. .................... 606/56 |
| 5,769,850 A | 6/1998 | Chin et al. |
| 5,772,661 A | 6/1998 | Michelson |
| 5,797,909 A | 8/1998 | Michelson |
| 5,807,382 A | 9/1998 | Chin |
| 5,810,812 A | 9/1998 | Chin |
| 5,810,827 A | 9/1998 | Haines et al. |
| 6,217,577 B1 * | 4/2001 | Hofmann ..................... 606/57 |
| 6,423,069 B1 * | 7/2002 | Sellers ........................ 606/71 |

* cited by examiner

SURGICAL DISTRACTOR FRAME

CROSS REFERENCE TO RELATED APPLICATION

The present disclosure claims the benefit of U.S. Ser. No. 60/342,963 filed Dec. 21, 2001, and which is hereby incorporated by reference.

TECHNICAL FIELD

This invention relates to distractors for use in surgery to repair broken, deformed or damaged bones and joints.

BACKGROUND INFORMATION

There have been various distractor systems developed, many of which in one form or another utilize a plurality of transfixing and/or half pins which extend through the bone and outward beyond the soft tissue surrounding the bone. The multiple pins are positioned on opposite sides of the fracture and rigidly attached to one or more pin couplings at their distal ends. The pin couplings are interconnected by at least one mounting bar which permits the bone portions located on opposite sides of the fracture to be repositioned relative one another. It is often necessary during surgery to repair broken, deformed or damaged bones and joints to distract tissue segments of interest to provide the proper alignment prior to positioning fixation elements. The distractors that must be utilized to overcome deforming compressive forces of contracted soft tissue may interfere with access to the surgical site in several ways. From a mechanical standpoint, the distraction frame may obstruct physical access to the patient's wound. Furthermore, from a visualization standpoint, the distraction frame may obstruct the surgeon's ability to see the surgical site and the ability to visualize the underlying tissue using X-ray imaging or other devices.

One example of prior art is disclosed in U.S. Pat. No. 4,220,146 to Cloutier, which is incorporated by reference into this Application in its entirety. Such a prior art distractor is illustrated in FIG. 1. The prior art distractor comprises an upper pin 102 which is introduced laterally through a patient's bone above a joint, for instance, into the femoral condyles 104a and 104b in a direction perpendicular to the long axis of the femur according to well known surgical procedures. A lower pin 106 is introduced laterally below the joint into the patient's tibia 108 through the soft tissue of the bone in a direction substantially parallel to that of the upper pin 102.

The upper and lower pins 102 and 106 are connected to each other on both sides of the femur 107 and tibia 108 by a pair of threaded rods 110a and 110b. Mounted to the threaded rod 110a, is a serrated wheel 112a. One leg 116a of an L-shaped member 114a is rotately coupled to the wheel 112a. The other leg 118a of the L-shaped member couples to the pin 106. The leg 118a is pierced by a cylindrical hole extending along its longitudinal axis. The cylindrical hole is of such a diameter as to receive a portion of the rod 110a in a slidable manner and to guide the same. In a similar manner, an L-shaped member 114b and wheel 112b couple the pin 106 to threaded rod 110b.

Adjustments in the vertical distance between the pins 102 and 106 can be made by turning the wheels 112a-112b along the threaded rods 110a and 110b. After the pins 102 and 106 are in place, turning the wheels 112a and 112b in a downward manner will induce compression stresses within the threaded rods 110a and 110b.

Because the rods 110a and 110b are relatively slender, the rods flex or buckle under compressive stresses. The buckling causes additional flexural stressed to develop within the rods. Furthermore, threads surrounding the exterior of the threaded rods 110a and 110b reduce the effective cross-sectional area of the rods and introduces residual stresses from threading process which further reduces the rod's structure strength.

Thus, there exists a substantial need for an improved distraction device adapted for intra-operative use.

SUMMARY OF THE INVENTION

The previously mentioned needs are fulfilled with the present invention. The present invention provides a distraction device that minimizes the obstruction of the surgical site while still providing the necessary distraction features to provide bone fragment alignment and overcome compressive forces of contracted soft tissue. In one aspect, the support member disposed over the surgical site is formed of a material that is substantially radiolucent such that underlying tissue may be readily imaged. Still further, the present invention provides a distractor frame that has an expansion mechanism axially displaced from the surgical site being distracted.

In one aspect of a preferred embodiment depicted herein for the purpose of illustration, there is provided a distractor frame, comprising an upper pin, a lower pin positioned substantially parallel to the upper pin, a pair of adjustment mechanisms, wherein each adjustment mechanism couples to the upper pin and the lower pin such that each adjustment mechanism is positioned generally perpendicular to upper and lower pins, wherein each adjustment mechanism comprises a shaft, a first means coupling the shaft for coupling the upper pin to the shaft, a threaded rod coupled to an end of the shaft, a cylindrical sleeve adapted for threadedly engaging the threaded rod, such that a portion of the shaft and a portion of the threaded rod may be positioned within the cylindrical sleeve, and a second means coupled to the cylindrical sleeve for coupling the lower pin. In a still further preferred aspect, at least the shaft is formed of radiolucent material.

These and other features, and advantages, will be more clearly understood from the following detailed description taken in conjunction with the accompanying drawings. It is important to note the drawings are not intended to represent the only form of the invention.

DETAILED DESCRIPTION OF THE INVENTION

Figure 1:
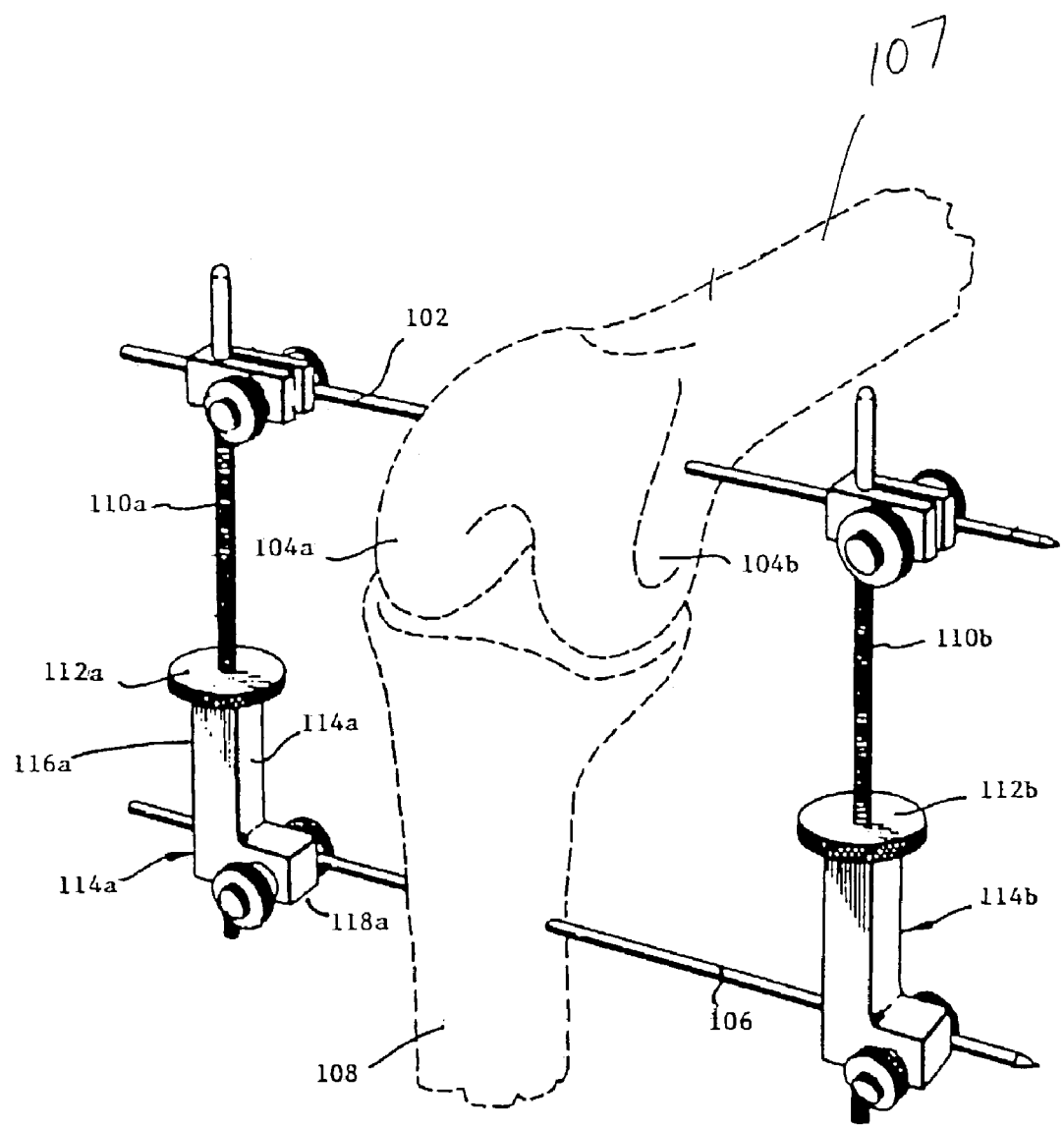
FIG. 1 is an isometric view illustrating a prior art device.
Figure 2:
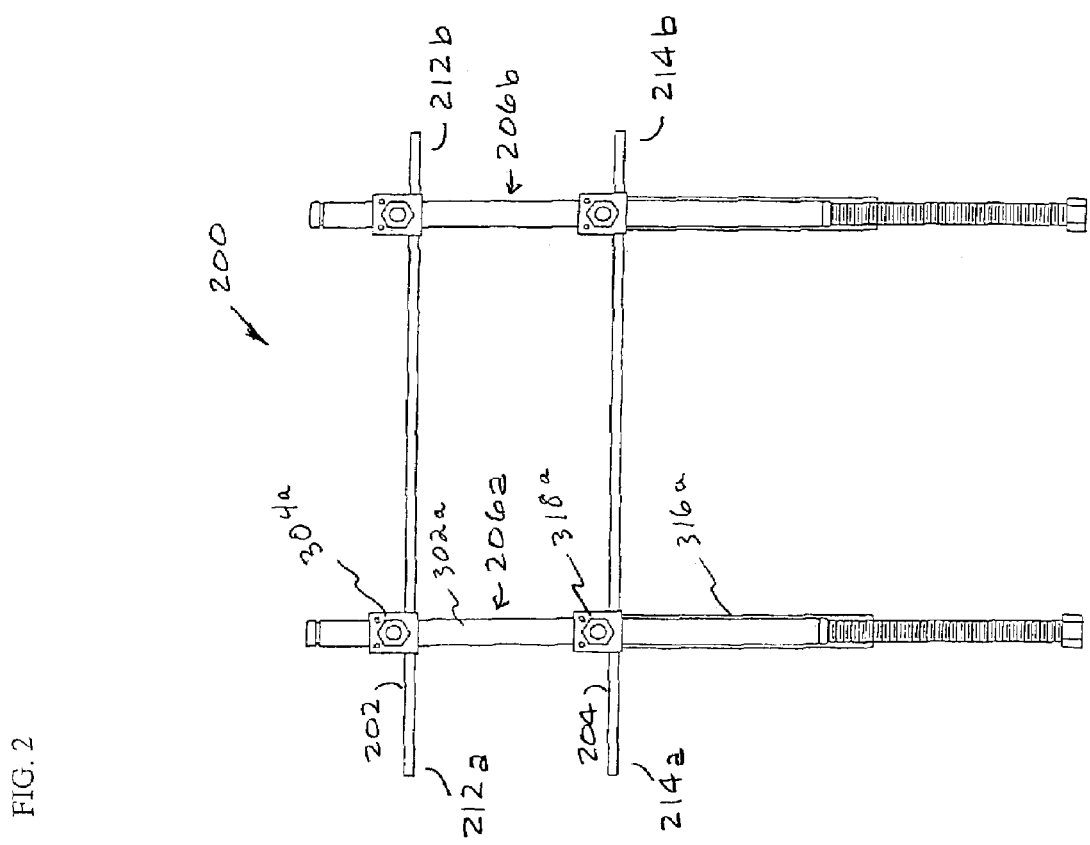
FIG. 2 is a partial cross-sectional top view of one embodiment of the present invention.
Figure 3:
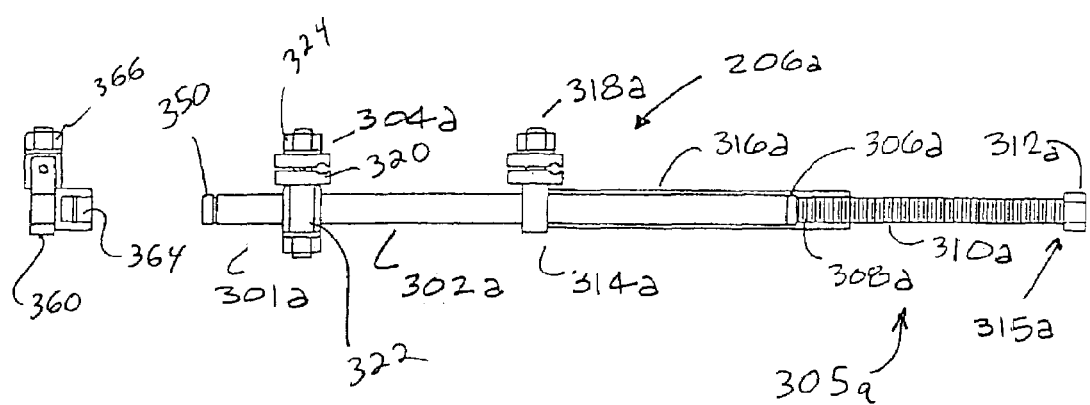
FIG. 3 is a partial cross-sectional side view of an embodiment of an adjustment mechanism used in the present invention.
Figure 4:
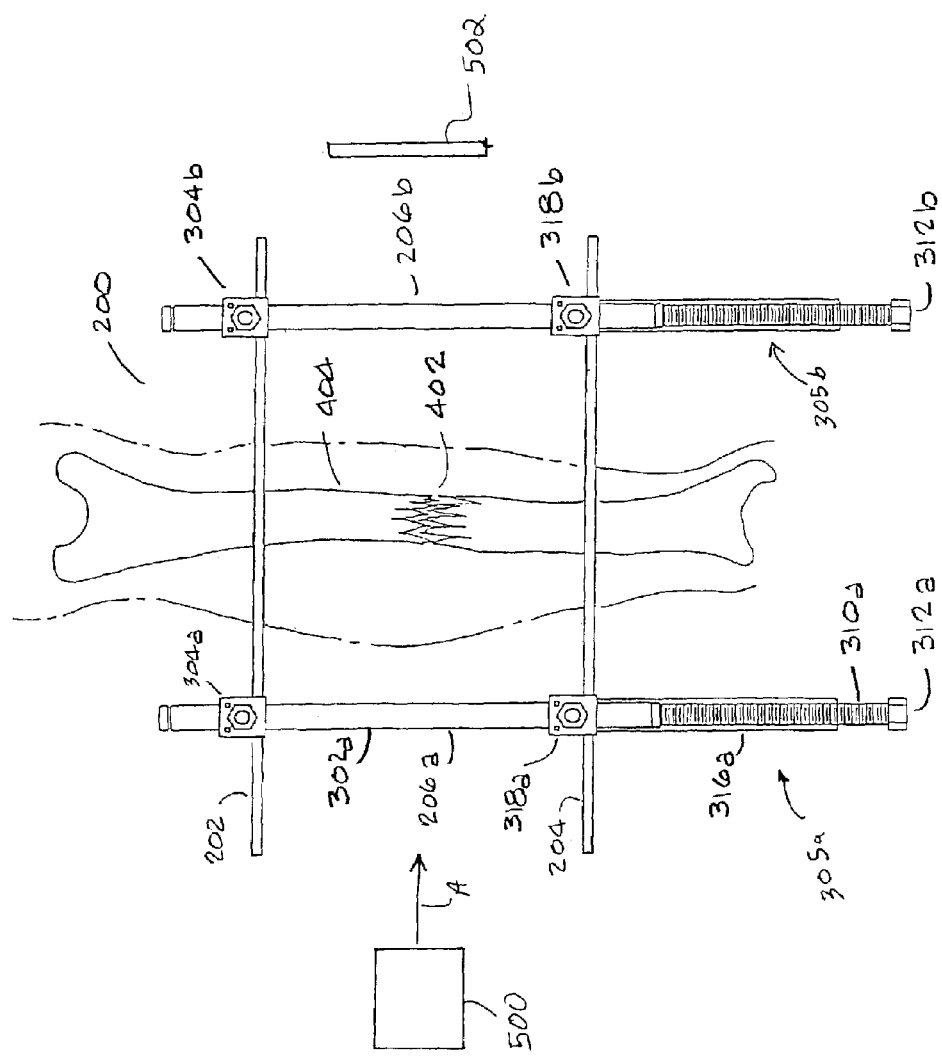
FIG. 4 is a partial cross-sectional top view of one embodiment of the present invention shown applied to a patient's leg.

The principles of the present invention and their advantages are best understood by referring to the illustrated embodiment depicted in FIGS. 2-4 of the drawings, in which like numbers designate like parts. In the following description, well-known elements are presented without detailed description in order not to obscure the present invention in unnecessary detail. For the most part, details unnecessary to obtain a complete understanding of the present invention have been omitted inasmuch as such details are within the skills of persons of ordinary skill in the relevant art. Details regarding mechanisms used to connect and control the rotation of the various elements described herein are omitted, as such mechanisms are within the skills of persons of ordinary skill in the relevant art.

Turning now to FIG. 2, there is illustrated one embodiment of an external distractor frame 200 in accordance with the principles of the present invention. The distractor frame 200 comprises a pair of upper and lower pins 202 and 204, and a pair of adjustment mechanisms 206a and 206b. The upper and lower pins 202 and 204, for example, may be conventional ³⁄₁₆ inch Steinmann pins. In the embodiment illustrated in FIG. 2, the upper and lower pins 202 and 204 are connected to each other by the adjustment mechanisms 206a and 206b, which are virtually identical to each other. The adjustment mechanisms 206a and 206b extend from the left and right ends 212a and 212b of the upper pin 202 to the left and right ends 214a and 214b of the lower pin 204, respectively. Turning now to FIG. 3, there is shown a side view of the adjustment mechanism 206a. The adjustment mechanism 206a comprises a main shaft 302a. At the first end 301a of the main shaft 302a, there is mounted a pin connector 304a for coupling the main shaft 302a to the pin 202. A first end 314a of a cylindrical sleeve 316a is coupled to a second pin connector 318a. The cylindrical sleeve 316a has an interior bore running through its longitudinal axis adapted to receive a portion of main shaft 302a. Pin connector 304 includes a rod clamp 320 having a passage to receive pin 202. Pin connector further includes a base assembly 322 coupled to main shaft 302a. It will be understood that nut 324 may be tightened to cause rod clamp 320 to tighten against pin 202 to thereby hold the relative positions. While a perpendicular relationship between pin 202 and shaft 302a is illustrated in FIG. 2, base assembly 322 and rod clamp 320 may be configured to permit angulations there between prior to tightening of nut 324 to accommodate a plurality of angular relationships during the distraction operation.

Adjacent the lower end of the main shaft 302a, there is an expansion mechanism 305a disposed between rod connector 304a and 318a. Coupled to the lower end of the main shaft 302a, there is a swivel connector 306a. The swivel connector 306a couples the main shaft 302a to a first end 308a of a threaded rod 310a. The swivel connector 306a allows the threaded rod 310a to rotate with respect to the main shaft 302a. A drive pattern 312a maybe fixedly coupled to a second end 315a of the threaded rod 310a. The drive pattern 312a, for example, may be a hexagon head adapted to be rotated by a hand tool. Alternatively, the turning mechanism could be a wheel or handle adapted to be directly rotated by a human hand.

The interior bore of sleeve 316a is threaded to mate with an exterior threaded surface of the threaded rod 310a. The interior bore has a diameter which is slightly larger than the exterior diameter of the main shaft 302a such that cylindrical sleeve 316a can slidably move in a longitudinal direction with respect to the main shaft 302a. Similarly, the second pin connector 318a also has an interior bore which is slightly larger than the exterior diameter of the main shaft 302a such the second pin connector 318a may slidably move with respect to rod 302a. However, the cylindrical sleeve 316a and second pin connector 318a may be restrained from free movement by threaded rod 310a which may be threadedly engaged the cylindrical sleeve 316a.

The adjustment mechanism 206b may have identical components to that of adjustment mechanism 206a, and as such will not be separately described. In one embodiment of the invention all of the components may be formed of medical grade stainless steel. In alternative embodiments, the components may be formed of alternative metals suited for medical applications. In a still further alternative embodiment of the present invention, one or more of the components is formed a material that is substantially passive in the presence of X-rays or energy emitted for nuclear magnetic resonance imaging (MRI). It is contemplated that the components of the device would have limited halo or occlusive effect in generating a visual image with imaging devices. Such materials may include medical grade plastics, composites, polymers, and metals not interfering with imaging devices. It is further contemplated that at least the components adjacent the surgical site be substantially radiolucent.

To illustrate the operation of the above described embodiment, assume the embodiment will be used to treat a fracture or osteotomy fragments of the tibia as illustrated in FIG. 4. In the this example, the upper pin 202 is introduced laterally above a fracture 402 occurring in the patient=s tibia 404 in a direction generally perpendicular to the longitudinal axis of the tibia. The lower pin 204 may be introduced laterally into the patient's tibia 404 below the fracture 402 through the soft tissue of the tibia in a direction substantially parallel to that of the upper pin 202. An optional appliance of a preliminary manual traction onto the pins to stretch the ligaments may be applied. In the illustrative embodiment, the pin connectors 304a, 304b, 318a, and 318b are screwed respectively to secure the pins 202 and 204 to the adjustment mechanisms 206a and 206b.

As shown in FIG. 4, fracture 402 is disposed between pins 202 and 204, and the respective pin connectors. Further, adjustment mechanisms 305a and 305b are axially displaced along the longitudinal axis of main shaft 206a and 206b, respectively, from the fracture 402. Thus, the adjustment mechanism is disposed away from the surgical site. Still further, drive patterns 312a and 312b are disposed on the distal ends of the adjustment mechanisms such that they are axially displaced from the fracture as far as possible. It will be understood that instruments necessary to engage the drive patterns 312a and 312b will similarly be located away from the surgical site. Thus, the surgeon may have an unobstructed view of and access to the patient's surgical site while the present invention is operated to distract the tissue of interest. Still further, in the preferred embodiment illustrated, only the main shaft 206a and 206b are disposed adjacent the fracture 402. This configuration minimizes the amount of components blocking physical and visual access to the surgical site.

Moreover, in a more preferred aspect, main shafts 302a and 302b are formed of substantially radiolucent material to permit visualization of fracture 402 with imaging equipment. While it is contemplated that the entire distractor may be constructed of radiolucent materials, in one preferred embodiment main shafts 302a and 302b are formed of medical grade plastic and the remaining components, including adjustment mechanisms 305a and 305b, are formed of medical grade metal. As illustrated in FIG. 4, an energy source 500, such as for example an X-ray source or MRI source, emits energy in the direction of arrow A. The energy passes substantially through main shaft 206a, is at least partially blocked by tissue adjacent fracture 402, passes substantially through main shaft 206b and is recorded at device 502. Thus, the recorded image may provide a substantially clear image of fracture 402 without undue interference from the distractor frame as the adjustment components are not in axial alignment with the energy path A of imaging equipment 500 and 502.

The turning mechanisms 312a and 312b may now be used to precisely adjust the distance between the upper pin 202 and the lower pin 204. For instance, rotating turning mechanism 312a will also cause the threaded rod 310a to rotate. Because the cylindrical sleeve 316a is threadedly engaged with the threaded rod 310a, the rotation of the threaded rod will cause the cylindrical sleeve 316a to move longitudinally with respect to the main shaft 302a. The lower pin 204 is coupled to the cylindrical sleeve 316a through the pin connector 318a. Thus, as the cylindrical sleeve 316a moves with respect to the main shaft 302a, the lower pin 204 will also attempt to move. Consequently, the rotation of the turning mechanisms 312a and 312b may apply traction onto the pins 202 and 204 until they are sufficiently separated to bring the bone fragments to the desired location and/or the ligaments are adequately taut. During this operation, the tension in the patient's ligaments may be checked by conventional methods, such as palpation. Radiographic images may be taken during the distraction process through the main shafts of the distractor frame to monitor the bone fragment distraction and alignment.

It is contemplated that in some applications the pin 202 may be replaced by a wire or cable that extends through a bone portion and is joined to the main shafts by connectors 304a and 304b. In this configuration, an additional coupler 360 may be added to end 350 of main shaft 302a and a similar coupler on main shaft 302b. A rigid rod may be connected between the two main shafts with the additional couplers 360. Main shaft end 302a is received in aperture 364 and nut 366 may be turned to tighten the coupler 360 onto the rod interconnecting the main shafts 302a and 302b. The interconnecting rod will maintain the relative alignment of the main shafts as force is applied to the flexible wire or cable.

Preferred embodiments of the distractor frame described above may be configured to have several advantages over the prior art, although all advantages may not be meet in different embodiments of the invention. Among other features and not a requirement of for the present invention, the primary structural members comprise a main shaft of substantially uniform diameter rather than a threaded rod. The main shafts 302a and 302b may have a greater cross-sectional area, which results in a larger section modulus and ultimately results in a shaft which is more rigid than a threaded rod of the same exterior diameter. The uniform diameter main shaft extending between the primary distractor connectors 304 and 318 provides a greater strength to diameter ratio because there are not surface features that may generate stress risers potentially leading to yielding or failure. Further, additional coupling components (not shown) may be provided to permit the surgeon to perform additional bone alignment procedures off the distractor frame of the present invention. Often bone fragments need to be aligned in multiple planes. Such components may have a uniform size since the diameter of the main shaft is constant along the length between the primary distraction couplers 304 and 318. The uniform diameter main shaft of the present invention also permits the attachment of further couplers to the main shaft without damage to the operation of the distractor, such as bending or deformation of the threads of the shaft that might be experienced in prior devices. Still further, the smooth main shaft permits infinite variability of the distance between the connectors 304 and 318 or any others that may be added later. This provides the distractor system of the present invention with a plurality of configurations to accommodate a wide range of medical indications.

As shown in FIGS. 2-4, the threaded shaft is only acting on the sleeve threads and the end of the main shaft. Thus, the threaded shaft that performs the work in the system is constrained within the outer sleeve to provide support. In this manner the complete distractor frame size may be reduced. An additional advantage is that the threaded shaft does not carry the compressive load experienced between the pin connectors along its axial length that extends outside the outer sleeve. Thus, this provides a system that is stronger in comparison to similarly sized components assembled in traditional fashion.

Many previous systems had the expansion mechanism that operate at right angles to the application of force. In the illustrated preferred embodiment of the invention, the hex nut is on the end and the surgeon can apply the rotational force directly in line with the axis of distraction. Since the applied force is substantially in axial alignment with the distractor main shaft, it is anticipated that a greater proportion of the applied force is translated into distraction force. Further, the hex nut is disposed on the end of the system making it easier to access and easier to fit a tool to end. A variety of tools can be used to engage the drive pattern including wrenches, ratchets and socket drives. It will be appreciated that the drive mechanism could be modified to an internal print within a socket or a feature that is manually operable without additional tools. Further, the expansion components are axially spaced from the surgical site to permit greater ease of access to the patient's fracture during the distraction procedure.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. Moreover, while a preferred embodiment has been described for use in treating a tibia fracture, such illustrative use is instructional only and is not intended to limit the applications of the present invention. By way of example, but without limitation to still further applications, the present invention may be applied to all long bones; heel, ankle and wrist fractures; as well as other joints including the spine, knee and shoulder. It is therefore, contemplated that the claims will cover any such modifications or embodiments that fall within the true scope of the invention.

I claim:

1. A surgical distractor frame adapted to distract at least two bone segments, the distractor comprising:
    an elongate shaft having an outer surface extending along a longitudinal axis and a first end and an opposite second end;
    an elongate sleeve having an internal bore with a distal end adapted to telescopingly receive said second end of said elongate shaft, and the elongated sleeve having an opposite proximal end;
    a first bone anchor adapted to engage a first bone segment and interconnected with said elongated shaft;

a second bone anchor adapted to engage a second bone segment and interconnected with said elongate sleeve proximate said distal end; and a rod telescopingly received within said proximal end of said elongated sleeve and in substantial alignment with said longitudinal axis of said elongated shaft disposed in the distal end of the elongated sleeve, said rod movable longitudinally within said sleeve to push against said second end of said elongated shaft to adjust the longitudinal distance between said first end of the elongated shaft and said distal end of the elongated sleeve to thereby adjust the distance between the first bone segment and the second bone segment;

wherein said rod includes a drive portion extending outside said proximal end of said elongated sleeve.

2. The distractor of claim 1, wherein at least said elongate shaft is formed of radiolucent material.

3. The distractor of claim 1, wherein said internal bore of said elongate sleeve defines a thread pattern and said rod is an externally threaded rod having a first rod end acting on said second end of said elongated shaft.

4. The distractor of claim 3, further including a swivel disposed between said first rod end and said second end of the said elongated shaft.

5. A surgical distractor frame adapted to distract at least two bone segments, the distractor comprising:

an elongate shaft having a first end and an opposite second end;

an elongate sleeve having an internal bore with a distal end adapted to telescopingly receive said second end of said elongate shaft;

a first bone anchor adapted to engage a first bone segment and interconnected with said elongated shaft;

a second bone anchor adaptable to engage a second bone segment and interconnected with said elongate sleeve;

an expansion mechanism disposed at least in part within said elongate sleeve, said expansion mechanism engaging said second end to adjust the distance between said first end and said distal end to thereby adjust the distance between the first bone segment and the second bone segment;

a swivel disposed between said expansion mechanism and said second end of the said elongated shaft; and wherein said elongate sleeve includes an opposite proximal end and said expansion mechanism includes a drive portion extending outside said proximal end.

6. The distractor of claim 5, wherein said internal bore of said elongate sleeve defines a thread pattern and said expansion mechanism is an externally threaded rod having a first rod end acting on said second end of said elongated shaft through said swivel.

7. The surgical distractor of claim 6, wherein said threaded rod includes a distal end spaced from said elongated sleeve, said distal end defining a drive pattern.

8. The surgical distractor of claim 7, wherein said drive pattern is in substantial axial alignment with said longitudinal axis.

9. The distractor of claim 5, wherein at least said elongate shaft is formed of radiolucent material.

10. The surgical distractor of claim 9, wherein said radiolucent material is plastic.

11. The surgical distractor of claim 5, wherein said elongate shaft has a substantially smooth surface.

12. A surgical distractor frame, comprising:

a distraction shaft having a first bone pin connector assembly configured for engagement with a bone pin;

a hollow sleeve having a first end, and receiving at least a portion of said distraction shaft within said first end, and an opposite second end including an internally threaded coupling, a second bone pin connector assembly attached to said hollow sleeve; and an externally threaded bolt threadedly engaging said internally threaded coupling of said hollow sleeve, said bolt being received within said hollow sleeve through said second end;

wherein threaded advancement of said bolt into said hollow sleeve telescopingly pushes a portion of said distraction shaft out of said sleeve thereby distracting said first bone pin connector assembly from said second bone pin connector assembly.

13. The frame of claim 12, wherein said distraction shaft is formed of a material including a medical grade plastic.

14. The frame of claim 12, wherein said distraction shaft is formed of a composite material not interfering with imaging devices.

15. The frame of claim 12, wherein said distraction shaft is substantially radiolucent.

16. The frame of claim 12, wherein said distraction shaft has a substantially smooth outer surface.

17. The frame of claim 12, wherein said distraction shaft has a first longitudinal axis and said bolt has a second longitudinal axis, said first and second longitudinal axes are in substantial alignment.

18. The frame of claim 17, wherein said distraction shaft is formed of a non-metallic material and said threaded bolt is formed of metal, and further including a bearing member disposed longitudinally between said distraction shaft and said bolt.

19. The frame of claim 18, wherein said bearing member is a swivel mounted to said distraction shaft.

* * * * *